United States Patent
Lo

[11] Patent Number: 6,089,241
[45] Date of Patent: Jul. 18, 2000

[54] DENTAL FLOSSER

[76] Inventor: Chen-Wan Lo, No. 21, Industrial 18 Rd., Taichung, Taiwan

[21] Appl. No.: 09/312,604

[22] Filed: May 17, 1999

[30] Foreign Application Priority Data

Dec. 7, 1998 [TW] Taiwan .................................. 87220409

[51] Int. Cl.⁷ .................................................... A61C 15/00
[52] U.S. Cl. ........................... 132/326; 132/327; 132/322
[58] Field of Search ..................................... 132/322, 323, 132/324, 325, 326, 327

[56] References Cited

U.S. PATENT DOCUMENTS

| | | | |
|---|---|---|---|
| 3,592,203 | 7/1971 | Johnson | 132/323 |
| 3,835,872 | 9/1974 | Daniel | 132/324 |
| 4,655,234 | 4/1987 | Bowden | 132/325 |
| 5,060,681 | 10/1991 | Westbrook et al. | 132/324 |
| 5,301,699 | 4/1994 | Craft | 132/323 |
| 5,348,032 | 9/1994 | Mason | 132/323 |
| 5,881,744 | 3/1999 | Lo | 132/325 |

*Primary Examiner*—Todd E. Manahan

[57] ABSTRACT

A dental flosser comprises a casing having a housing at one end for holding a supply of floss; a bent floss outlet section at the other end of housing forming an arc; an end hole in outlet section; a connecting rod disposed in casing between two ends; a slant body on front end of connecting rod; a flexible rod disposed in a channel in casing between ends thereof and having a slant groove connected with slant body of connecting rod; a switch connected to rear end of connecting rod including a protruding rod which is received in a hole in connecting rod; and a spring connected to casing and rear end of connecting rod. The tension of this flosser is adjustable and the flosser is free from external contamination.

8 Claims, 5 Drawing Sheets

DENTAL FLOSSER

FIELD OF THE INVENTION

The present invention relates to a dental device and more particularly to a dental flosser in which the tension is adjustable and is free from external contamination.

BACKGROUND OF THE INVENTION:

FIG. 1 shows a prior art dental flosser made of plastics and shaped like a knife. A pair of parallel supports 1 and 2 extended downwardly are used for tightening a segment of floss 3. The top elongated member is used as a handle 4. Its structure is very simple and thus becoming a popular dental flosser set nowadays. However, it is inconvenient to user because of the following reasons:
1. It is disposable and the sharp end of plastic handle 4 may hurt the user and/or other people inadvertently.
2. In use, the dental flosser 3 between the supports 1 and 2 is susceptable to breakage when the gap between teeth is very narrow.

It is common that people do not bring a number of flossers while going out. Thus such use-and-throw away flosser is not ideal. As an end, people still do not like to bring flossers when going out despite extensive efforts made by dental hygienists.

SUMMARY OF THE PRESENT INVENTION

It is an object of the present invention to provide a dental flosser comprising a connecting rod for providing a floss with desired tension.

It is another object of the present invention to provide an improved dental flosser which receives most of the floss therein for preventing the floss from being stained by external contamination.

It is still another object of the present invention is to provide an improved dental flosser comprising a cutting unit which can readily cut off the used portion of the floss in order to keep the dental floss clean.

The above and other objects, features and advantages of the present invention will become apparent from the following detailed description taken with the accompanying drawings.

DETAILED DESCRIPTION OF THE PREFERRED EMBODIMENT

Figure 1:
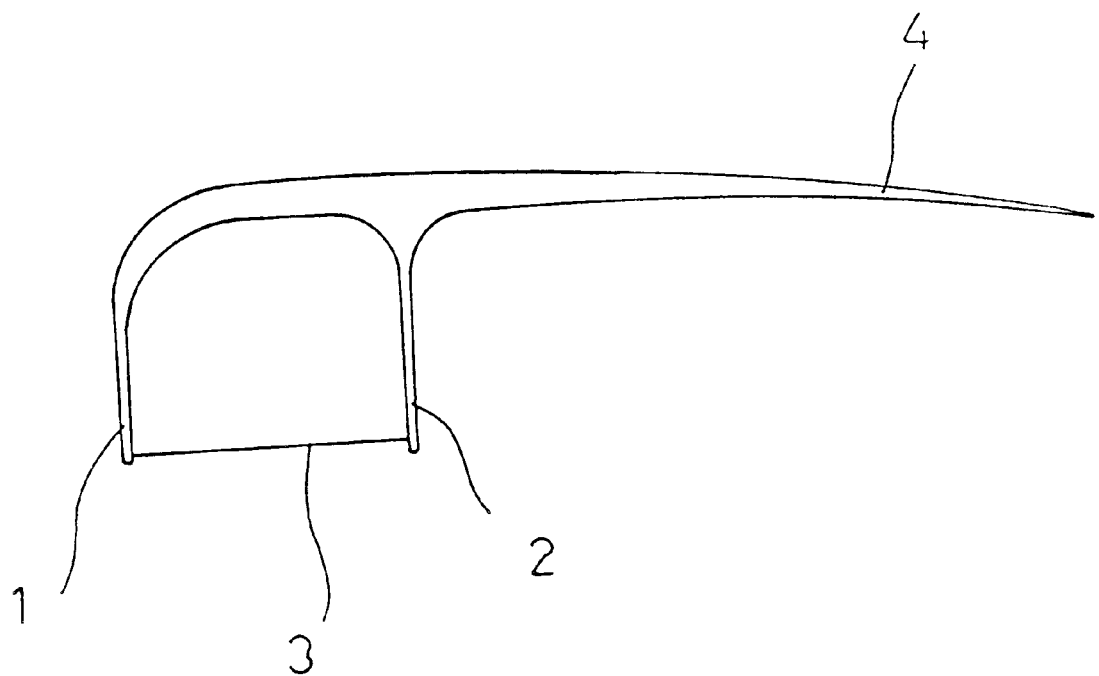
FIG. 1 is a side view showing a prior art dental flosser.
Figure 2:
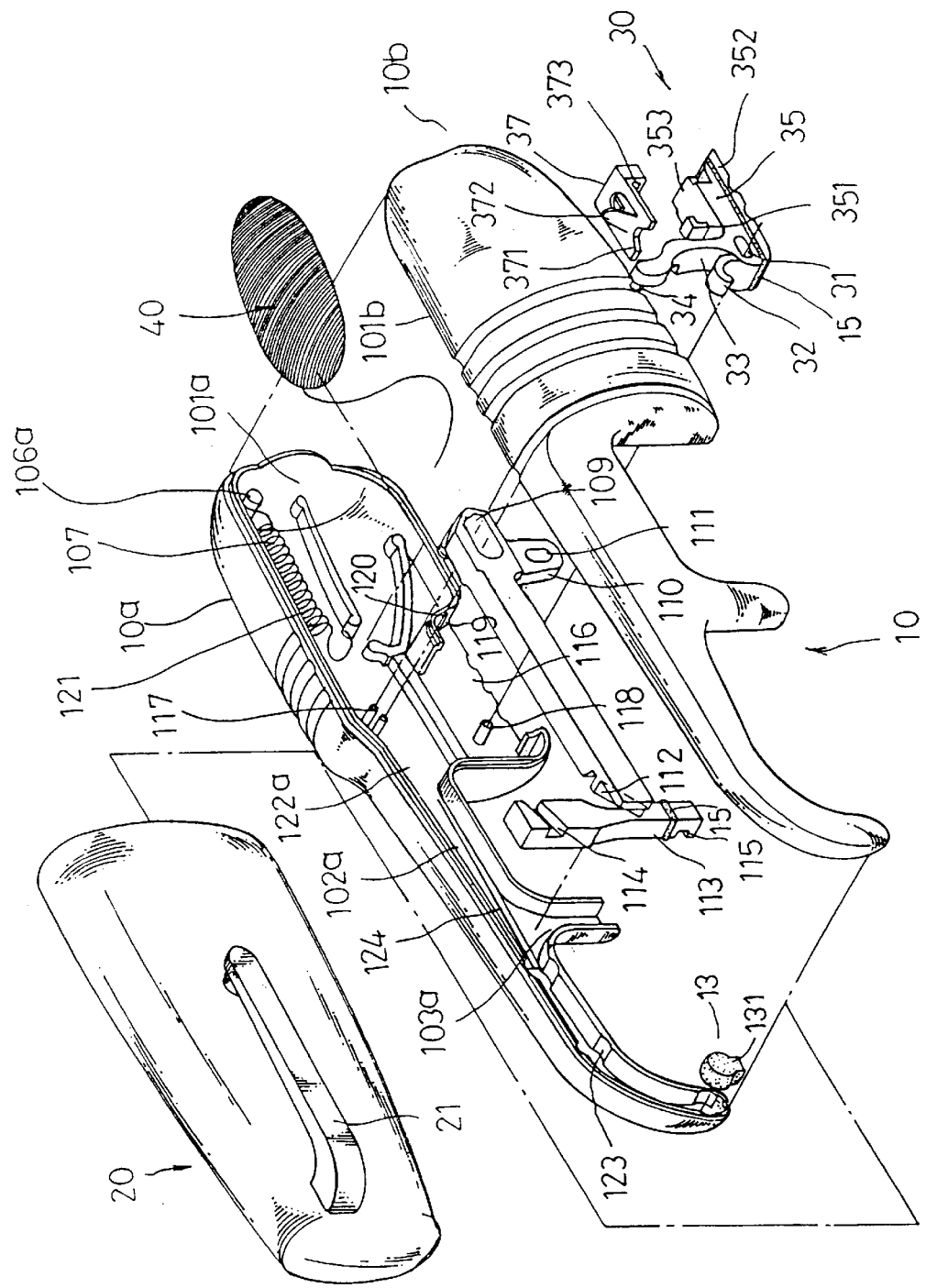
FIG. 2 is an exploded perspective view showing a preferred embodiment of the present invention.
Figure 3:
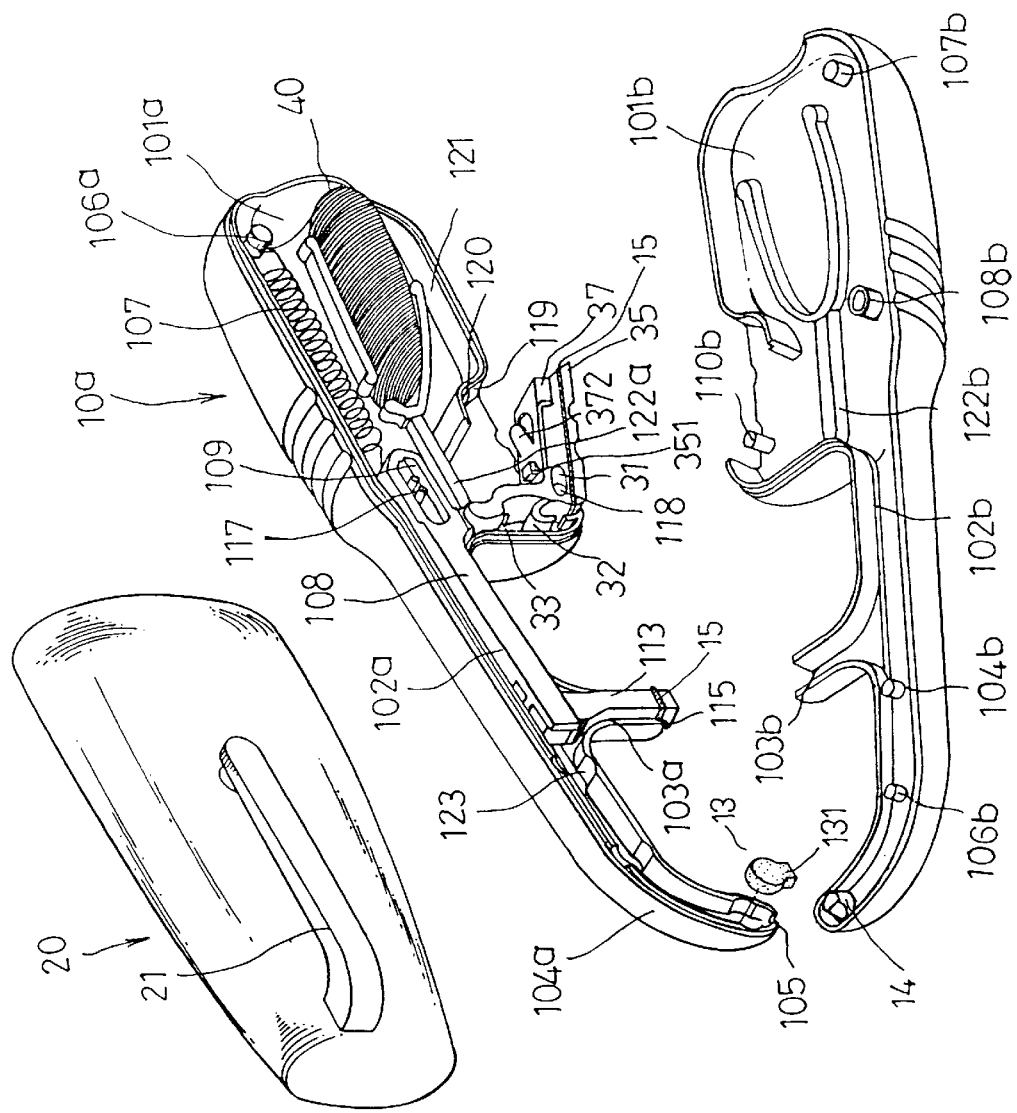
FIG. 3 is a perspective view showing a partially assembled dental flosser of the present invention.

With reference to FIGS. 2 and 3, the dental flosser of the present invention comprises a casing 10 and a clip-on cap 20 wherein the casing 10 of a generally E-shaped section consisting of a pair of symmetrical halves and an upper half portion 10*a* and a lower half portion 10*b* made of plastics. In the rear part of the upper half portion 10*a* there is a housing 101*a*. In the middle portion of the upper half portion 10*a* there is a sliding channel 102*a*. Under the sliding channel 102*a* and parallel to the sliding channel 102*a* is provided a dental floss groove 124. The sliding path 102*a* extends downward to form a channel 103*a*. The front of the upper half portion 10*a* is designed to bend downward like an arc. In hollowed middle part of the upper half portion 10*a* lies an arc floss groove 102*c*. An end arc portion corresponding to the lower half portion 10*b* forming a tiny hole 105 below the front of the casing 10. In the housing 101*a* of upper half portion 10*a*, a protruding pole 106*a* is provided. A spring 107 is inserted in to the hole of the protruding pole 106*a* wherein one end inserted in the hole of the protruding pole 106*a* and the other end is hooked in the rear end of a connecting rod 108. The rod 108 is positioned in the middle section of the sliding channel 102*a* of the casing 10. A hole 109 is provided on the rear end of the connecting rod 108. A protruding body 110 with a connecting hole 111 thereon is provided under the hole 109. The thickness of the rear portion of the connecting hole 111 is about one half of that of the front part of the connecting rod 108. On the front end of the connecting rod 108 a slant body 112 is formed. More specifically, the slant body 112 is a protruding strip slanted downward, The slant body 112 is assembled with astrip-shaped flexible rod 113 being fixed by the channel 103*a* of the upper half portion 10*a*. A slant groove 114 is provided on the upper part of the flexible rod 113 to connect with the slant body 112 of the connecting rod 108. A seam 115 is provided on the lower end of the flexible rod 113. After the upper half portion 10*a* and the lower half portion 10*b* have been attached together, an opening 116 is formed at the bottom thereof. A pair of guide rods 117 are provided on the upper wall and a pin 118 is provided on the lower wall of the casing 10. The pin 118 is used for mounting a switch 30. A lock point 120 is provided on the rear wall of the opening 116. On the lower part of the switch 30 a hole 31 is provided, while on its front part an elastic body 32 is formed. Above the elastic body 32 there is a protruded trigger 33 with a pin 34 on its top side for inserting into the connecting hole 111 on the lower part of the connecting rod 108. The thickness of the upper part of the trigger 33 is one half of that of its lower part. The rear part of the switch 30 is a platform 35. A latch 351 is provided on top of the platform 35. A protrusion 353 is provided on the rear end of the platform 35. A metal blade member 37 is put on the upper part of the platform 35. In front of the blade member 37 is a recess 371. The latch 351 of the switch 30 is inserted into the recess 371 for being secured therein. Above the blade frame 37 is a sharp blade 372 extended backward. Behind the blade 372 is a rectangular fixing groove 373. Beneath the platform 35 a locking point 352 protrudes. A groove 354 is provided at the end of platform 35.

A member 121 is provided on the inner surface of the upper half portion 10*a*. A rib 122*a* is provided in the inner wall of housing 101*a*. In front of the channel 103*a* of the upper half portion 10*a* there are a plurality of the engaging grooves 123.

The shape of the lower half portion 10*b* mates with that of the upper half portion 10*a* wherein a housing 101*b* is provided in the rear part, and a sliding channel 102*b* is provided in the middle portion. The sliding channel 102*a* bends downward to form a channel 103*b*. The front part of the channel 102*a* bends downward to form a semicircular concave arc on its bottom. Therefore, when the upper half portion 10*a* and the lower half portion 10*b* are attached together there is a tiny hole 105 formed at the tip. There are a plurality of fastening rods 106*b* spaced apart in the front part of the lower half portion 10*b*. An elastic rod 107*b* is provided in the rear housing 101*b* of the lower half portion 10*b*. Again, there is a floss-pressing rod 108*b* provided on the upper part of the inner wall of the lower half portion 10*b*.

Meanwhile, a rib 122*b* is provided at a position in the lower half portion 10*b* corresponding to that of the rib 122*a* in the upper half portion 10*a*. Near the opening 116 of the lower half portion 10*b* there is a fixing rod 110*b* corresponding to the pin 118 in the upper half portion 10*a*.

The Cap 20 is a sleeve member corresponding to that of the front part of the upper half portion 10*a*. The cap 20 covers the front part of the casing 10 with a clamp 21 put on its outer surface.

A water-proof block 13 made of elastomeric material is provided adjacent an end of arc floss groove 102*c*. Waterproof block 13 has a raised portion 131 protrude into tiny hole 105 for preventing water from permeating into casing 10 for causing contamination. A rod member 14 is provided in the inner surface of lower half portion 10*b*. The rod member 14 urges against waterproof block 13 to keeping waterproof block 13 in place. One side of member 14 is slant, thereby enabling supply of floss 40 to pass therethrough. Then supply of floss 40 pass between waterproof block 13 and member 14 to the outside of casing 10 via the tiny hole 105. A waterproof peripheral flange 15 made of elastomeric material is secured on strip-shaped flexible rod 113. The flange 15 is located between seam 115 and stripshaped flexible rod 113 abutted the walls of channels 103*a*, 103*b* for preventing water from permeating into casing 10. A similar flange is provided in switch 30 for preventing water from permeating into casing 10.

To assemble the apparatus, a spool is first put in between the clamps 12, i.e., between the upper and lower parts of the upper half portion 10*a*. Then the floss is pulled upwardly to pass through the central portion between guide poles 117. Then pass through the dental floss groove 124 beneath the sliding channel 102*a* in the front of the upper half portion 10*a*. The dental floss is further pulled to the arc floss groove 102*c* in the front of the upper half portion 10*a*. Then is pulled through the tiny hole 105 at the tip. Then the flexible rod 113 is put in the channel 103*a* of the upper half portion 10*a*. The connecting rod 108 is put on the sliding channel 102*a* in the upper half portion 10*a*. The slant body 112 of the connecting rod 108 is put in the slant groove 114 provided on the upper part of the flexible rod 114. The front end of spring 107 is inserted into the rear hole 109 of the connecting rod 108 and is hooked therein. The rear end of the spring 107 is inserted into the hole of protruding rod of the upper half portion 10*a*. The pin 118 of the upper half portion 10*a* is inserted into the hole 31 of the switch 30. The pin 34 of the trigger 33 of the switch 30 is inserted into the connecting hole 111 of the connecting rod 108. Finally, the lower half portion 10*b* is attached to the upper half portion 10*a*. At this time the fixing rod 110*b* of the lower half portion 10*b* is inserted in the hole 31 of the switch 30 in such a way that one half of the hole 31 is occupied by the fixing rod 110*b* and the other half is occupied by the pin 118 of the upper half portion 10*a*. The elastic rod 107*b* of the lower half portion 10*b* presses on the circular surface of the protruding rod 106*a* of the upper half portion 10*a* to cause the rear end of the elastic body 107 to be secured therein. The hole of the floss-pressing rod 108*b* of the lower half portion 10*b* is allowed to contain both the guide rods 117 of the upper half portion 10*a*. Hence the floss-pressing rod 108*b* is capable of pressing the supply of floss 40 to cause it to move forward horizontally, between guide rods 117 of the upper half portion 10*a*, along the dental floss groove 124. The joined part of the protruding body 110 of the connecting rod 108 and the trigger 33 of the switch 30 is clamped by the ribs 122*a* and 122*b* of the upper half portion 10*a* and lower half portion 10*b* respectively. The fastening rods 106*b* on the front of the lower half portion 10*b* just lies in the engaging grooves 123 on the front of upper half portion 10*a*. The flexible rod 113 is clamped by the channels 103*a* and 103*b* of the upper half portion 10*a* and the lower half portion 10*b* respectively.

Figure 4:
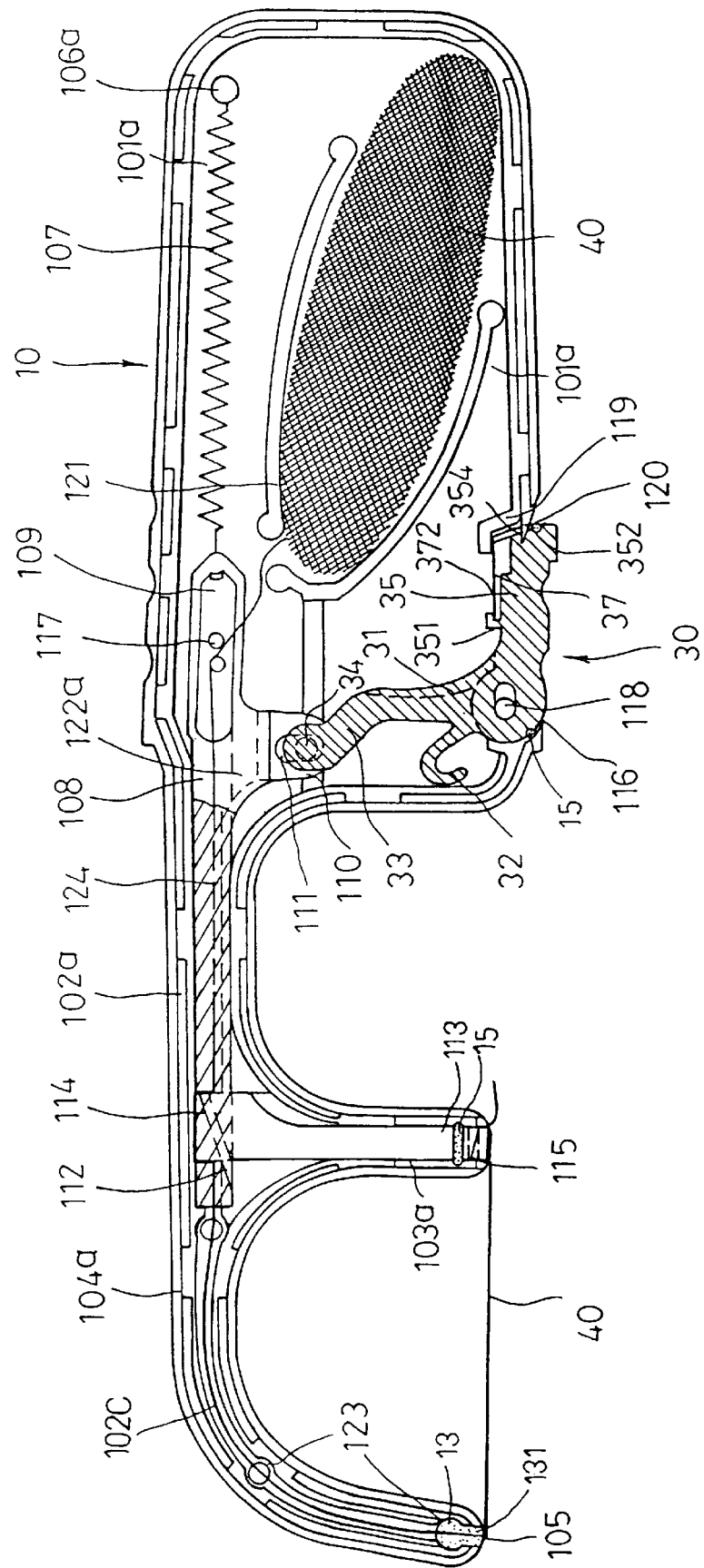
FIGS. 4 and 5 are side views showing an assembled dental flosser of FIG. 2 and an opened switch respectively.

After the upper half portion 10*a* and lower half portion 10*b* have been attached together, the supply of floss 40 is pulled out through the tiny hole 105 at the tip of arc formed by the downward extended front part of the upper half portion 10*a*. Then it moves forward and winds around the seam 115 below the flexible rod 113. In operation, if the bottom of the switch 30 and the bottoms of housings 101*a* and 101*b* lie in a transversal line as shown in FIG. 4. Then the dental flosser of the invention is ready for use for removing food particles from between the teeth. At this time, the end tip of the flexible rod 113 is drawn back to the casing 10 and is clamped by the surfaces of the channels 103*a* and 103*b*. Hence the supply of floss 40, which wound around the seam 115, is pushed upward by the flexible rod 113 and limited by the surfaces of channels 103*a* and 103*b*. As such, it wouldn't fall off. The end of the supply of floss 40 being pulled out lies between the flexible rod 113 and the wall surfaces of the housings 101*a* and 101*b* of the casing 10. Now the supply of floss 40 on top of the flexible rod 113 will be pushed up and clamped by the upper, left and right walls of the channel 103*a* of the casing 10*a*. The flexing rod 113 clamps the supply of floss 40 with both its upper end and lower end. As a result, the supply of floss 40 is ready for use.

Figure 5:
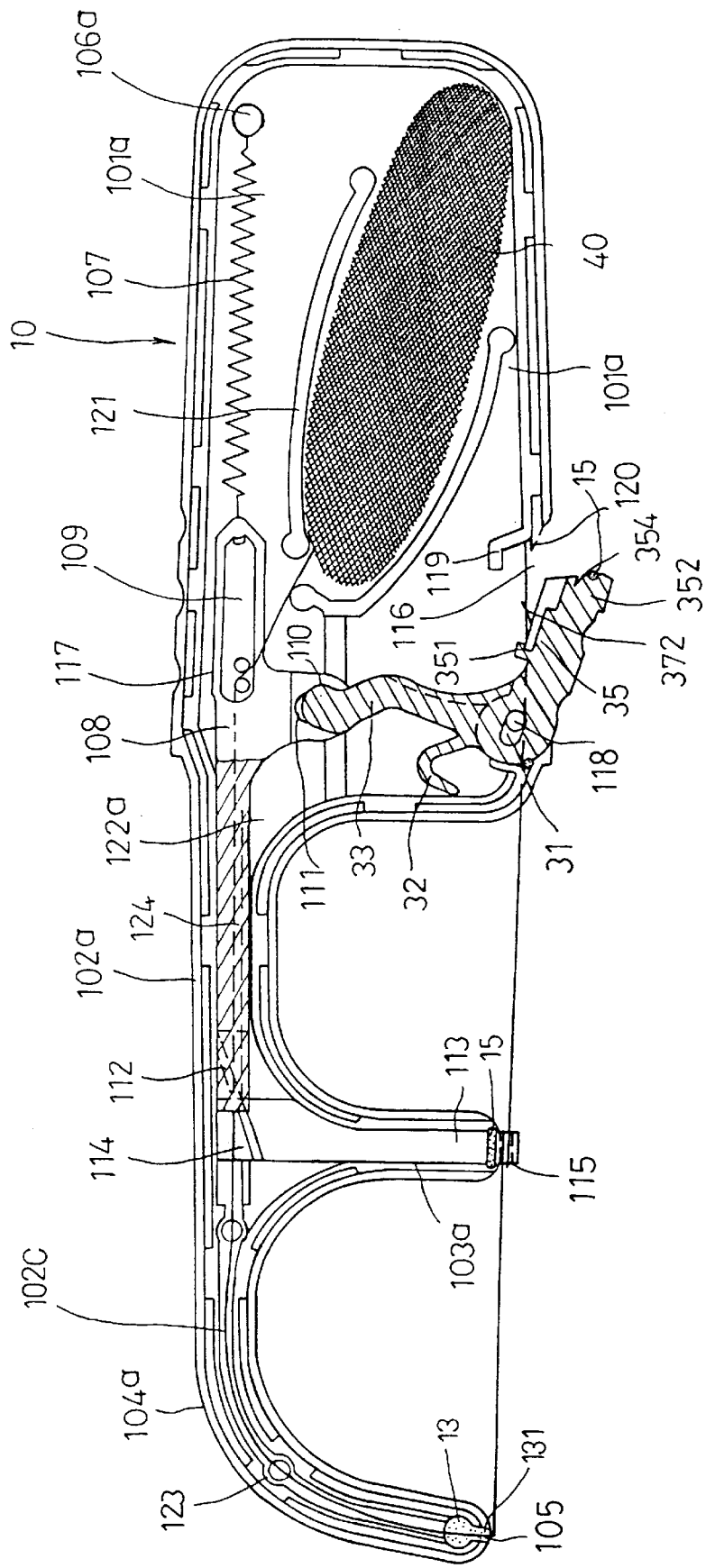

In order to clean food particles from between the teeth with the supply of floss 40, first the locking point 352 of the switch 30 is pushed down and the platform 35 is pushed forward to cause the hole 31 to move backward. At this time the platform 35 lies flat. The groove 354 separates the lock point 120 from the wall of the opening 116 of the casing 10. Now the switch 30 is pushed downward to turn clockwise about pin 118 to an angle of about 15 to 22 degrees as shown in FIG. 5. The trigger 33 on the upper part of the switch 30 rotates clockwise simultaneously about 15–22 degrees to drive the pin 34 to rotate, while the pin 34 pushes the connecting rod 108 to move backward. As such, this push force combines with the tension of the spring 107 on top of the housing 101*a* will cause connecting rod 108 to move back significantly. As the slant body 112 on the front of the connecting rod 108 is inserted in the slant groove 114 of the flexible rod 113, once the connecting rod 108 moves backward, the slant body 112 will drive the flexible rod 113 to move downward. This is achieved by utilizing the relative motion of the upper and lower edges of the slant body 112 of the connecting rod 108. The slant groove 114 of the flexible rod 103 may produce a force to push the flexible rod 113 to move downward to make the seam 115, wound in the supply of floss 40, exposed at the opening on the bottom of the channels 103*a* and 103*b* of the casing 10. Then the dental floss is loosened and a used section is pulled out. The supply of floss 40 is passed through the guide pole 117, the dental floss groove 114, and the fine hole 105 at the tip of the casing 10, to the bottom edge of the opened blade 372. The used section of the supply of floss 40 is cut by blade 372 and a section of the clean supply of floss 40 is again wound on the seam 115 of the flexible rod 113. The switch 30 is pushed into the casing 10 again. At this time the groove 354 on the rear of the switch 30 is put under the lock point 120. The trigger 33 on the upper part of the platform 35 is moved to normal position. The connecting rod 108 is pushed by the pin 34 of the trigger 33 to return to its original position. The front slant body 112 of the connecting rod 108 is forced to drive the flexible rod 113 moving upward. Thus the supply of floss 40 wound on the seam 115 of the flexible rod 113 is drawn back into the channels 103a and 103b of the casing 10. The end of the supply of floss 40 clamped by the facings of the channels 103a and 103b is fixed so that it wouldn't fall off. Note that once the upper half portion 10a and the lower half portion 10b of the present invention are attached together, the fastening rods 106b will insert into the engaging grooves 123 of the upper half portion 10a for pressing on the supply of floss 40. As such, it will move along the bottom of the arc floss groove 102c. The pressing rod 107b in the rear housing 101b of the lower half portion 10b will press upon the protruding rod 106a of the upper half portion 10a. As such, the tip of the spring 107 presses in the hole of the protruding rod 106a to keep in place. The ribs 122a and 122b of the upper half portion 10a and the lower half portion 10b will clamp the joined portion of the connecting rod 108 and the trigger 33 of the switch 30. The pin 118 in the housings 101a and 101b of the lower half portion 10b and the fixer 110b are put in the hole 31 of the switch 30 on the left side and right side respectively to keep switch 30 in place. The casing 10 is covered with cap 20 on its front and is adapted to clamp on the pocket of user's clothes for achieving the purpose of convenient carry.

While the invention herein disclosed has been described by means of specific embodiments, numerous modifications and variations could be made thereto by those skilled in the art without departing from the scope of the invention set forth in the claims.

What is claimed is:

1. A dental flosser comprising:
   a casing having a housing at one end for holding a supply of floss;
   a bent floss outlet section at the other end of the housing forming an arc;
   a hole in the distal end of the outlet section;
   a connecting rod disposed in the casing between the two ends;
   a slant body on the front end of the connecting rod;
   a vertical flexible rod disposed in a channel in the casing between the ends thereof and having a slanted groove connected with the slanted body of the connecting rod;
   a switch connected to the rear end of the connecting rod including a protruding rod which is received in a hole in the connecting rod; and
   a spring connected to the casing and the rear end of the connecting rod.

2. The dental flosser as recited in claim 1, wherein the slant body coordinates with the slant groove to slide downwardly, the thickness of the front end of the connecting rod is smaller than that of the rear end thereof, and the thickness of the upper end of the flexible rod is smaller than that of the lower end thereof.

3. The dental flosser as recited in claim 1, wherein the switch has a shape adapted to be grasped by hand and a blade provided on top of the switch.

4. The dental flosser as recited in claim 1, further comprising a clamp on the outer surface of the housing for positioning and guiding the supply of floss.

5. The dental flosser as recited in claim 1, wherein the rear end of the connecting rod extends out downwardly to form a protrusion with a hole thereon, the switch has a trigger with a pin provided on the upper end of the switch, the pin inserts into the hole of the connecting rod, the upper end of the trigger is thinner than the lower end thereof, and the lower end of the protrusion of the connecting rod is thinner than the upper end thereof.

6. The dental flosser as recited in claim 5, further comprising a plurality of ribs in the housing for securing the joined portion of the protrusion of the connecting rod and the trigger of the switch.

7. The dental flosser as recited in claim 1, further comprising a block adjacent the end of the arc having a raised portion protruded into the hole of the outlet section for preventing water from permeating into casing, a member provided in the casing for urging the block in place having a slant side, thereby enabling the supply of floss to pass between the block and the member, the hole of the outlet section to outside of the casing.

8. The dental flosser as recited in claim 1, further comprising a pair of peripheral flanges secured on the flexible rod and the switch respectively for preventing water from permeating into the casing.

* * * * *